United States Patent
Denney

(10) Patent No.: US 11,460,409 B1
(45) Date of Patent: Oct. 4, 2022

(54) METHODS AND REAGENTS USEFUL FOR VERIFICATION OF THE INTEGRITY OF A URINE SAMPLE AND THE DETECTION OF COUNTERFEIT URINE

(71) Applicant: Vision Diagnostics, Inc., Branford, FL (US)

(72) Inventor: Jerry W. Denney, Branford, FL (US)

(73) Assignee: VISION DIAGNOSTICS, INC., Branford, FL (US)

( * ) Notice: Subject to any disclaimer, the term of this patent is extended or adjusted under 35 U.S.C. 154(b) by 119 days.

(21) Appl. No.: 15/961,003

(22) Filed: Apr. 24, 2018

Related U.S. Application Data

(60) Provisional application No. 62/501,849, filed on May 5, 2017.

(51) Int. Cl.
| | | |
|---|---|---|
| *G01N 21/78* | (2006.01) | |
| *G01N 33/493* | (2006.01) | |
| *C12Q 1/42* | (2006.01) | |
| *G01N 21/77* | (2006.01) | |
| *G01N 33/487* | (2006.01) | |
| *G01N 21/75* | (2006.01) | |

(52) U.S. Cl.
CPC .............. *G01N 21/78* (2013.01); *C12Q 1/42* (2013.01); *C12Y 301/03001* (2013.01); *C12Y 301/03002* (2013.01); *G01N 33/4875* (2013.01); *G01N 33/493* (2013.01); *G01N 2021/752* (2013.01); *G01N 2021/7759* (2013.01); *G01N 2021/7769* (2013.01); *G01N 2021/7793* (2013.01)

(58) Field of Classification Search
CPC .. G01N 21/78; C12Q 1/42; C12Y 301/03001; C12Y 301/03002
See application file for complete search history.

(56) References Cited

U.S. PATENT DOCUMENTS

| | | | | |
|---|---|---|---|---|
| 5,057,435 A * | 10/1991 | Denney | ................. | G01N 33/84 |
| | | | | 436/79 |
| 5,981,206 A * | 11/1999 | Arter | ................. | C12Q 1/42 |
| | | | | 435/21 |
| 2011/0118141 A1* | 5/2011 | Pugia | ................. | G01N 33/54386 |
| | | | | 506/9 |
| 2017/0010276 A1* | 1/2017 | Chen | ................. | G01N 33/6827 |

FOREIGN PATENT DOCUMENTS

WO  WO-2015130225 A1 * 9/2015 ............. G01N 33/70

OTHER PUBLICATIONS https://en.wikipedia.org/wiki/Chromophore (Year: 2021).*
https://en.wikipedia.org/wiki/Chromogen (Year: 2021).*
https://en.wikipedia.org/wiki/Thymolphthalein (Year: 2021).*
Venkatratnam et al., "Zinc Reduces the Detection of Cocaine, Methamphetamine, and THC by ELISA Urine Testing", Journal of Analytical Toxicology, vol. 35, Jul./Aug. 2011 (Year: 2011).*
Welsh et al., "Novel Spot Tests for Detecting the Presence of Zinc Sulfate in Urine, a Newly Introduced Urinary Adulterant to Invalidate Drugs of Abuse Testing", Am J Clin Pathol 2013;140:572-578 (Year: 2013).*
Daniel, O. et al., "Urinary Excretion of Acid Phosphastase," *British Medical Journal*, Jan. 2, 1954, pp. 19-21.
Gault, M.H. et al., "Clinical Significance of Urinary LDH, Alkaline Phosphatase and Other Enzymes," *Canad. Med. Ass. J.*, 1969; pp. 208-215, vol. 101.
Guo, W. et al., "DNA Verified Sample Authenticity for Urine Drug Testing Results from early commercial experience with a new method for matching submitted urine samples to specific patients," Postgraduate Medicine, 2016, pp. 35-36, vol. 128, No. S2.
Samilpa, P. et al., "Synthetic Urine How Easy is it to find, order and have synthetic urine delivered," Postgraduate Medicine, 2016, pp. 78-79, vol. 128, No. S2.
Combating cheating in urine drug testing, [online, webpage, retrieved Sep. 11, 2018] from: https://blog.employersolutions.com/combatting-cheating-in-urine-drug-testing/, p. 1.

* cited by examiner

*Primary Examiner* — Ruth A Davis
(74) *Attorney, Agent, or Firm* — Saliwanchik, Lloyd & Eisenschenk

(57) ABSTRACT

The problem of detecting whether a urine sample is true human urine or a counterfeit urine product is solved by the use of reagent systems that detect two markers normally present in human urine. The markers acid phosphatase and alkaline phosphatase catalyze the substrates thymolphthalein monophosphate and p-nitrophenol phosphate, respectively. These substrates are formulated as spot tests on a dip stick or as reagents for use in automated chemical analyzers. The presence of the markers can be qualitatively detected by color-changes in the sample, formed by the pH-specific chromogens that result from catalysis of the substrates with the markers. The control reagent can further indicate whether a counterfeit urine product contains one or both of the chromogens.

15 Claims, 5 Drawing Sheets
(3 of 5 Drawing Sheet(s) Filed in Color)

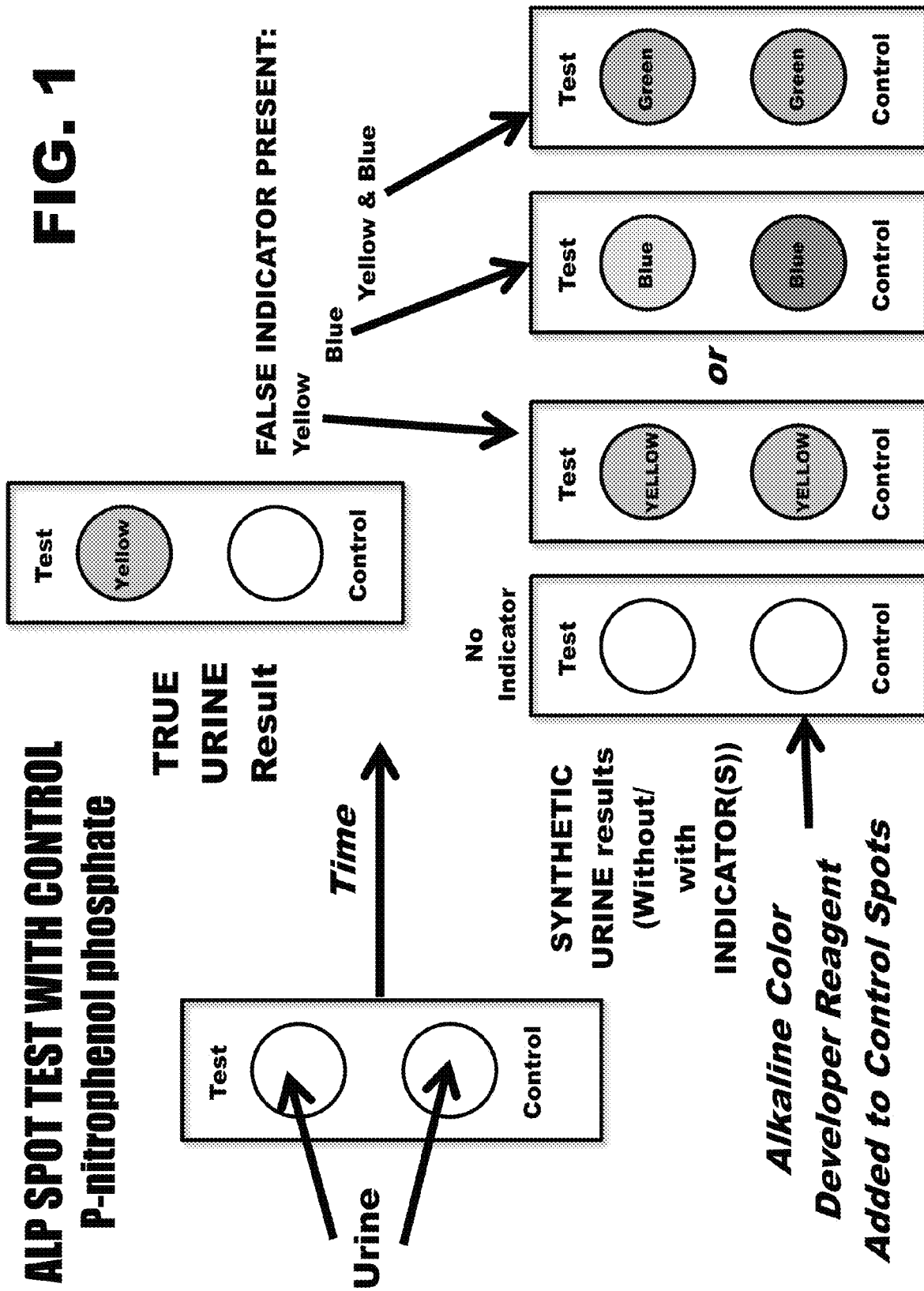

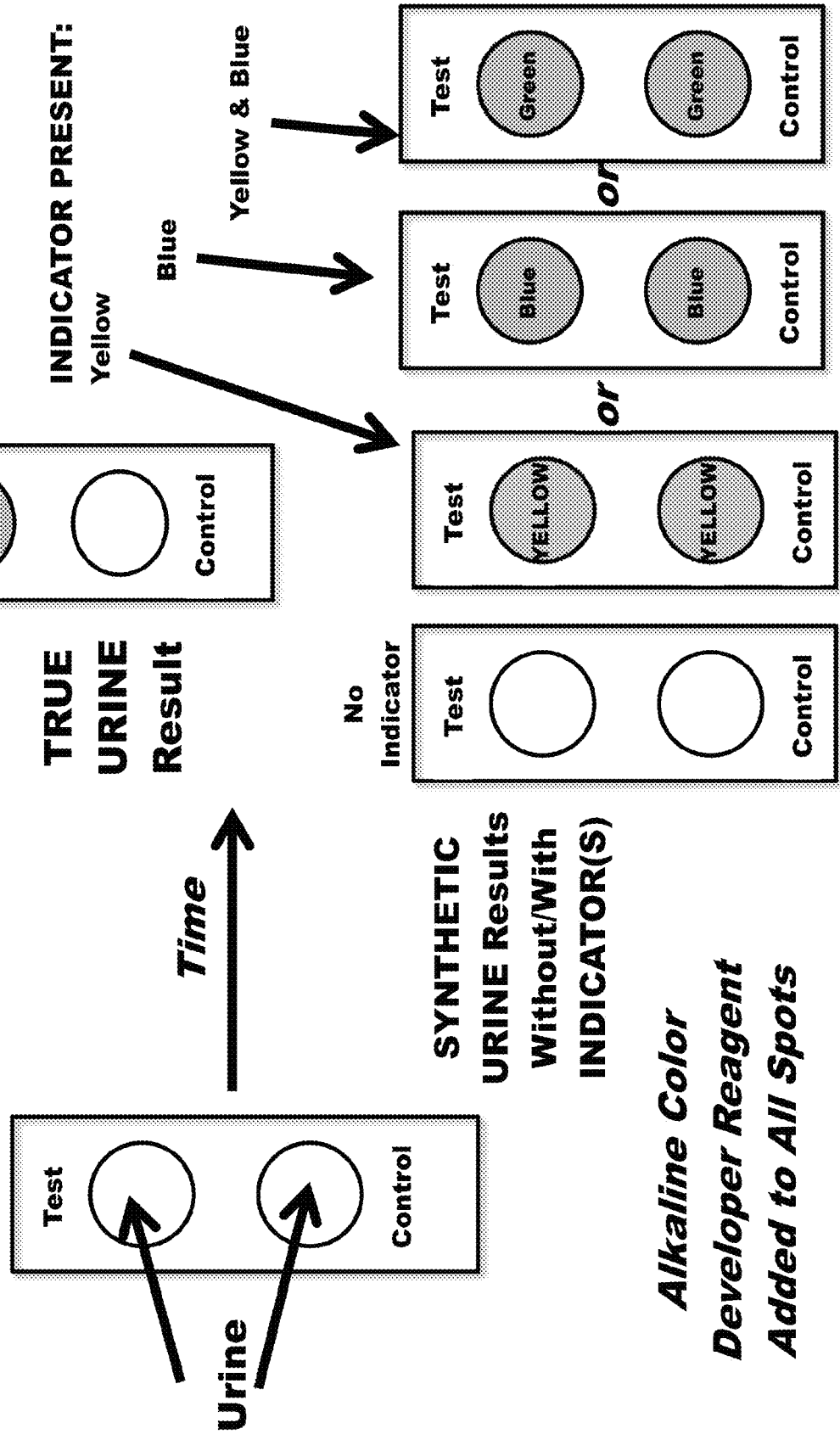

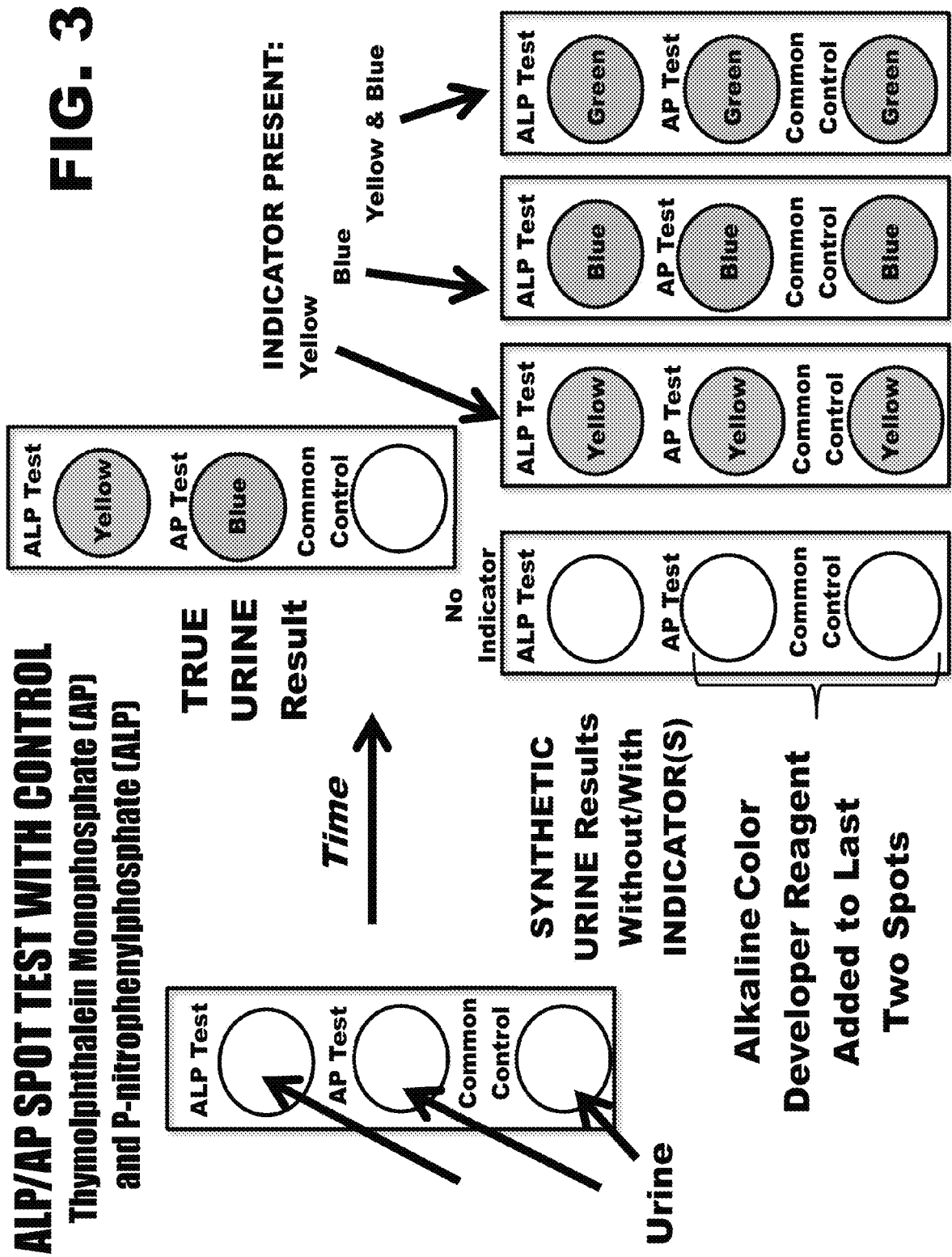

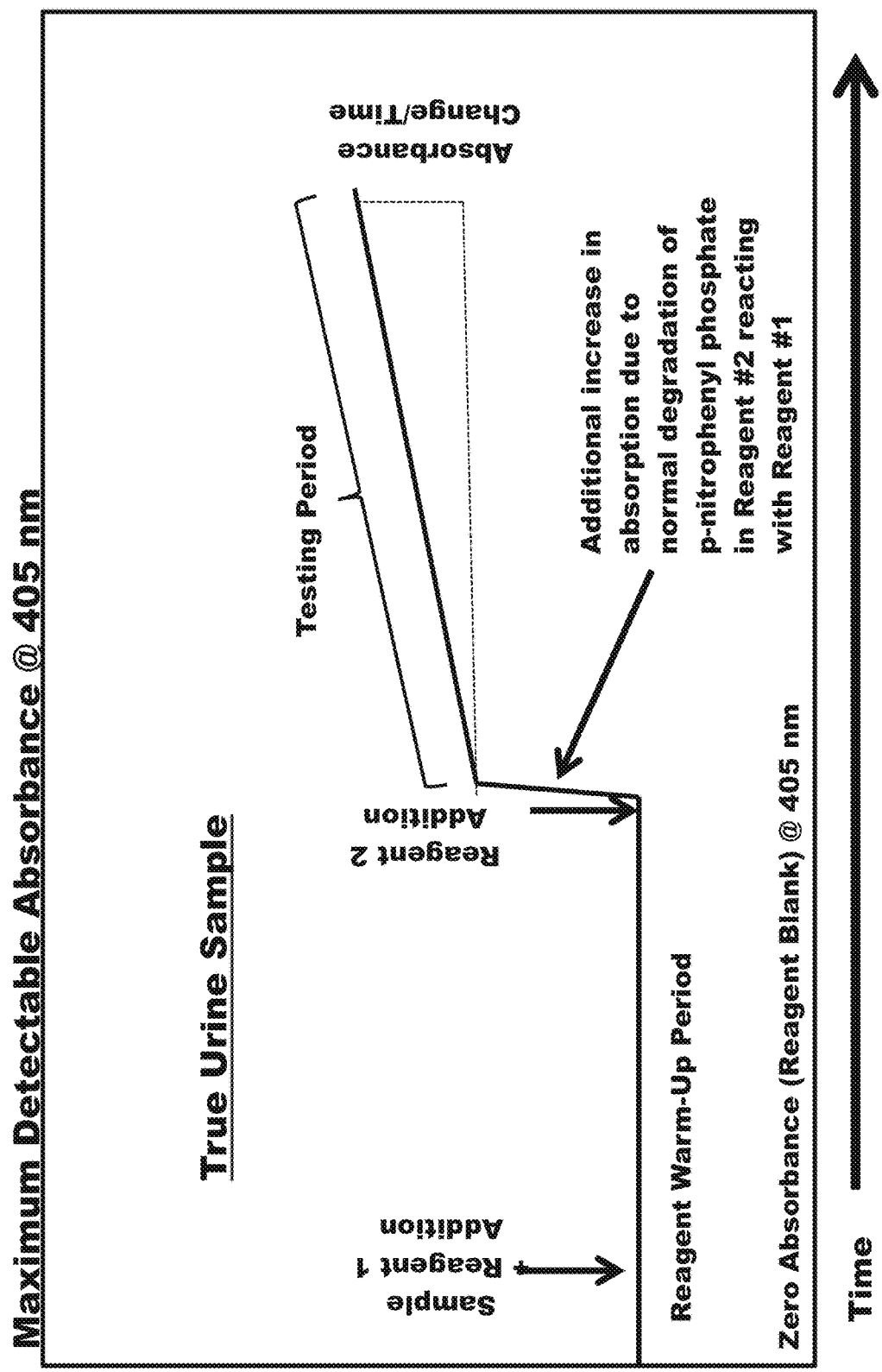

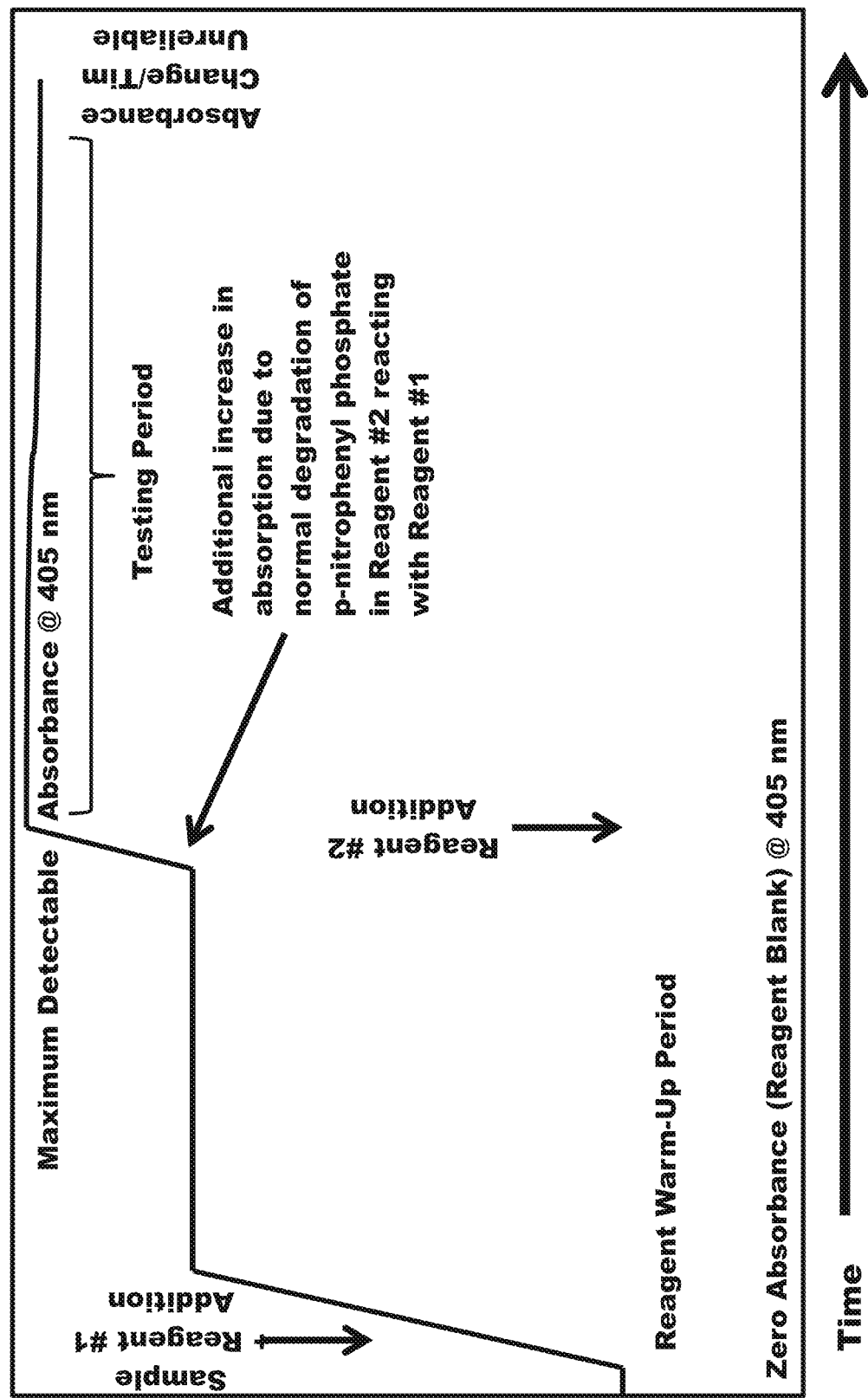

METHODS AND REAGENTS USEFUL FOR VERIFICATION OF THE INTEGRITY OF A URINE SAMPLE AND THE DETECTION OF COUNTERFEIT URINE

CROSS-REFERENCE TO A RELATED APPLICATION

This application claims the benefit of U.S. Provisional Application Ser. No. 62/501,849, filed May 5, 2017, the disclosure of which is hereby incorporated by reference in its entirety, including all figures, tables and drawings.

BACKGROUND OF INVENTION

Illegal drug use is damaging to both society and the drug users. The current level of drug use has become a significant national security issue, with opioid addiction being reported as a national epidemic. According to a recent report by the Centers for Disease Control and Prevention (CDC) there has been a 200% increase in the rate of opioid overdose deaths between 2000 and 2014. With the rapid increase in drug use, testing for drugs-of-abuse (DOA) has taken on a new significance.

Testing usually involves several steps, including: (a) sample collection, (b) testing sample integrity, (c) performance of DOA screening tests, and (d) performance of confirmatory tests. Each of these steps may: (a) occur at different locations, (b) be conducted by personnel of varying qualifications, (c) be conducted by different institutions or laboratories, and (d) be conducted after significant time intervals. For example, the performance of confirmatory tests is usually conducted after the screening tests are performed and often necessitate transport of a sample from one institution or laboratory to another. The multiple steps required when testing for DOA can occur over three or more days, meaning that the confirmatory testing step, if necessary, may be performed several days after collection of a sample.

A variety of tests are available and regularly used for detecting sample tampering or adulteration of samples submitted for DOA testing. These tests typically rely on detecting and measuring constituents in urine, or obtaining measurements of specific characteristics of a urine sample, such as the temperature, specific gravity, and/or pH. If the constituent or characteristic is outside the normal range, or below the Federal mandated cut-off level for human urine, adulteration can be suspected. The sample can be subjected to additional more specific tests or, alternatively, further testing on the sample can be halted and another sample obtained. Even though the additional test can be more specific, it cannot detect DOAs that have been destroyed and, in which, a false negative result is likely. Therefore, testing should be halted when adulteration is detected.

These tests are usually unreliable for determining whether the sample being tested is a counterfeit urine product. Counterfeit urine products are made to contain all of the constituents normally found in urine and that are tested for in most DOA testing laboratories. They are also calibrated to have a pH and specific gravity similar to true urine and can be presented for testing by techniques that present the sample at or about a normal body temperature. When employed with the standard tests for DOA, counterfeit urine product can be an effective mimic for true, human-derived, urine.

For at least the past twenty years, adulteration and dilution of urine samples have been effectively used as means of avoiding detection of DOA, despite the sample integrity testing methods currently in use. New testing methods are developed to try to counter efforts to adulterate, dilute or otherwise mask DOA in urine samples. It is likely that increased efforts and improvements in detection of the common dilution and adulteration methods of subverting drug tests will lead to increased use of counterfeit urine products, which have historically been effectively used to avoid detection of DOA with sample-integrity testing techniques.

Counterfeit urine products can be substituted for a human-derived urine sample by various subversive means. While a number of states have passed laws banning counterfeit urine products, they are still relatively easy to acquire. The market for these products has been estimated to be approaching $1 billion and continues to grow. A recent study showed that an internet search can yield hundreds, if not thousands, of counterfeit urine products that can be received within days. [Sampilpa, P. and Langley, L., "Counterfeit Urine: How Easy is it to find, order and have counterfeit urine delivered," Postgraduate Medicine 2016; 128: 78-79].

Counterfeit urine products contain most of the substances assayed in human-derived urine, including, for example, creatinine, urea, sodium, potassium, calcium, magnesium, chloride, phosphate, uric acid, ascorbic acid, and proteins. The pH, specific gravity, as well as levels of creatinine and other ingredients are adjusted to be within normal human ranges and concentrations. As such, counterfeit urine products can be effective in subverting most DOA tests.

To date, there have been no reports of human DNA being added to counterfeit urine products. Procedures have been introduced for detecting counterfeit urine products by using DNA detection techniques. While these methods are promising, they can be expensive to implement, in both technical labor and specialized reagents. Furthermore, DNA verification techniques do not lend themselves for use in the automated analyzers commonly used in testing laboratories. [Guo, W., Rhodes, R., and Sampilpa, P., "DNA Verified Sample Authenticity for Urine Drug Testing Results from early commercial experience with a new method for matching submitted urine samples to specific patients," Postgraduate Medicine 2016; 128: 35-36].

Most testing laboratories utilize commercial automated analyzers that allow large numbers of samples to be quickly analyzed, which can reduce the costs of the tests. Nonetheless, the costs associated with conducting tests to detect DOA in urine are still significant and most laboratories perform only a few tests that have been historically reliable in detecting the common DOA. With the ongoing improvements in methods and substances for subversion of such tests and the expected resulting increase in the use of counterfeit urine products, additional tests need to be developed and multiple tests performed on individual samples.

There is a particular need for techniques and procedures to quickly and inexpensively detect counterfeit urine samples. More particularly, there is a need for methods and products that can detect one or more constituents that are unique to human-derived urine and that are not added to counterfeit urine products. It would be most beneficial if such methods and products could be implemented as both a dip stick test, for quick on-site testing, and as one or more reagents useful in automated analyzers to allow for faster, more cost effective sample testing.

BRIEF SUMMARY

In accordance with the subject invention, the problem of determining whether a urine sample submitted for drugs-ofabuse (DOA) testing comprises "true urine"—being human-derived—or a counterfeit urine product is solved by methods and reagents capable of detecting in a sample at least one marker that is unique to true urine. More specifically, the reagent systems and testing methodology of the subject invention can confirm whether a sample is true urine by measuring one or more protein substances typically present only in true urine.

The embodiments of the subject invention are unique in their ability to detect the absence of a constituent in the sample, rather than the presence of a constituent, as an indication that the sample is not true human urine. Embodiments of the subject invention employ two different markers normally found in urine. Advantageously, the markers utilized with the testing methodology of the subject invention are activated and/or detectable under significantly different conditions. A further advantage of these markers is their labile nature that makes them impractical to use as additives in counterfeit urine products. Furthermore, while efforts can be made to mimic the presence of these markers, such as by addition of indicator dyes, the embodiments of the subject invention can be used to detect such efforts.

Specifically, embodiments of the subject invention utilize the labile markers acid phosphatase (AP) and alkaline phosphatase (ALP) to detect whether urine is "true urine," being of human origin, or is a counterfeit urine product. AP and ALP are preferred enzyme markers because they are present in urine produced by both males and females and have poor in vitro stability.

In a further embodiment, the subject invention utilizes the chromogenic substrates thymolphthaleine monophosphate and p-nitrophenyl phosphate, which are catalyzed by AP (at pH 4-6) and ALP (at pH 8-10), respectively. Thymolphthalein monophosphate and p-nitrophenyl phosphate are advantageous because they are catalyzed at significantly different pH levels, but produce chromogens that are activated under identical alkaline conditions. The subject invention utilizes this advantageous characteristic to create a single test control for detecting the presence of both of these chromogens.

The subject invention provides a testing methodology utilizing a dual reagent system that can detect the presence of one or both of the markers with a clear qualitative change in the state of the sample. More specifically, the presence of the markers forms chromogens from substrates in the reagents and imbue the sample with a clearly identifiable color. The urine markers are not detectable by current methods for testing sample integrity, such as, for example, pH, creatinine, specific gravity, oxidant, and aldehydes tests. The markers are temperature sensitive, which makes them unstable after sample collection, often degrading in a sample within 3 days, in the case of Acid Phosphatase, and in about a week to 10 days in the case of Alkaline Phosphatase. Most commercial DOA testing products recommend that tests be performed within 3 days of urine sample collection, when stored at ambient temperature or, if refrigerated, within 5 days of urine sample collection. Nonetheless, testing laboratories often test all samples received regardless of the time since collection or the conditions under which they were handled and stored. Advantageously, performing both acid and alkaline phosphatase assays, according to embodiments of the subject invention, can provide an indication of sample age. With the dual reagent system testing methodology of the subject invention, a negative acid phosphatase result and a positive alkaline phosphatase result can be an indication that the sample is true urine, but has undergone improper handling and/or storage. Testing laboratories are required to assess their handling and storage procedures to ensure that sample test results are accurate. The embodiments of the subject invention can provide a system and method for providing such validation for laboratories.

The time frame of 3-5 days is usually sufficient for most testing laboratories to complete a standard testing regimen, but is too long a time-frame for practical addition of the AP and ALP markers to most counterfeit urine products. Such products are usually stored and shipped at ambient temperatures and may be weeks or months old at the time of use, by which time these labile markers will have disappeared in the product.

When the substrates are combined with an aliquot of a true urine sample, the AP and ALP in the urine cleaves the respective phosphate moiety from the substrates, thereby producing free thymolphthaleine and free p-nitrophenol, respectively. Formation of the thymolphthalein chromogen requires acidic conditions, whereas formation of the p-nitrophenol chromogen requires alkaline conditions. In embodiments of the subject invention, the p-nitrophenol activated by ALP is self-indicating, such that the color appears as the chromogen forms. Subsequently changing the pH of the sample with an alkaline reagent activates the free thymolphthaleine to turn blue. A sample containing both of these markers causes the colors to combine and turns the sample green (combination of the blue and yellow colors) under alkaline conditions.

A preferred embodiment of the subject invention incorporates a control that lacks the substrates and both chromogens. With this embodiment, any subsequent change in the color of the control indicates that a sample is a counterfeit urine product or was otherwise subject to tampering. For example, the control can turn blue or yellow, as described above, or, alternatively, can turn green indicating that both of the chromogens were added to the sample and were not naturally occurring.

These distinctive color changes can be advantageous for use as a dip stick test, as well as for use in automated chemical analyzers, which can be reliably calibrated to ensure accurate, reliable, and consistent results. When this method is employed utilizing spectrophotometric automated chemical analyzers, the blue color is absorbed near 600 nm and the yellow color is absorbed at about 410 nm. Both techniques provide simple qualitative results.

BRIEF DESCRIPTION OF DRAWINGS

The patent or application file contains at least one drawing executed in color. Copies of this patent or patent application publication, with color drawing(s), will be provided by the Office upon request and payment of the necessary fee.

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention.

FIG. 1 illustrates a method for detecting the presence of alkaline phosphatase in a urine sample, according to embodiments of the subject invention. The method is illustrated utilizing a dip stick with a Test spot comprising p-nitrophenyl phosphate substrate to which a sample can be added and that, according to embodiments of the subject invention, reacts with alkaline phosphatase (ALP) in true urine to form the chromogen p-nitrophenol. The control has neither the substrate nor the chromogen. P-nitrophenol turns yellow at the alkaline pH necessary for the ALP, if present in the sample, to catalyze the p-nitrophenyl phosphate substrate. When an alkaline pH reagent is added to the Control spot, the sample can be counterfeit urine if it also turns dark yellow indicating that p-nitrophenol was present in the sample and was not formed as a result of alkaline phosphatase in the urine. It can also be seen in this Figure that if the thymolphthalein chromogen was added to the sample, the Test spot, as well as the Control spot turn blue, due to the alkalinity of both spots. Further, if both chromogens were added to the sample, the Test spot and the Control spot turn green, a result of the combination of both chromogen colors.

FIG. 2 illustrates a method for detecting the presence of acid phosphatase in a urine sample, according to embodiments of the subject invention. The method is illustrated utilizing a dip stick with a Test spot comprising a thymolphthalein monophosphate substrate to which the sample can be added and that, according to embodiments of the subject invention, react with acid phosphatase (AP) present in true urine to form the chromogen thymolphthalein. Thymolphthalein is colorless at the acid pH necessary for the AP, if present in the sample, to catalyze the thymolphthalein monophosphate substrate. The Control spot has neither the substrate, nor the chromogen. When an alkaline pH reagent is added to the Test spot and the Control spot, the chromogen formed at the Test spot is activated and imparts a blue color to the Test spot. The Control spot can indicate whether the sample is counterfeit urine if it also turns blue, indicating that thymolphthalein was present in the sample and was not formed as a result of acid phosphatase in the urine. It can also be seen in this Figure that if the p-nitrophenol chromogen was added to the sample, the Test spot, as well as the Control spot turn yellow. Further, if both chromogens were added to the sample, the Test spot and the Control spot turn green, a combination of both chromogen colors.

FIG. 3 illustrates a method for detecting the presence of both acid phosphatase (AP) and alkaline phosphatase (ALP) in a sample, according to embodiments of the subject invention. The method is illustrated utilizing a dip stick with one spot comprising p-nitrophenyl phosphate substrate (labeled as ALP) and another spot comprising thymolphthalein monophosphate substrate (labeled as AP), as well as a third Control spot containing neither of the substrates, nor their chromogens. According to embodiments of the subject invention, when true urine is added to the Test spots, the substrates react with either the alkaline phosphatase (ALP) or acid phosphatase (AP) to form the respective chromogens p-nitrophenol and thymolphthalein. If the sample is true urine, the ALP Test spot turns yellow and the AP Test spot and Control spot remain colorless. When an alkaline pH reagent is added to the AP Test spot and the Control spot, the AP Test spot turns blue and the Control spot remains uncolored. The Control spot indicates a counterfeit sample if it turns either blue or yellow, indicating that the chromogen was likely added to the sample and was not formed as a result of alkaline or acid phosphatase in the urine. If the control turns green, it indicates that both chromogens were added to the sample and were not formed as a result of alkaline or acid phosphatase in the urine. It can also be seen that if either chromogen was added to the sample, all of the Test spots, as well as the Control spot turn yellow and/or blue. Further, if both chromogens were added to the sample, all of the Test spots and the Control spot turn green, a combination of both chromogen colors.

FIG. 4 is a graph illustrating an embodiment of a p-nitrophenyl phosphate reagent system utilized to analyze a true urine sample utilizing liquid reagents in a chemical analyzer.

FIG. 5 is a graph illustrating an embodiment of a p-nitrophenyl phosphate reagent system utilized to analyze a counterfeit urine sample with added indicator dye.

DETAILED DISCLOSURE

The subject invention provides testing procedures for detecting, individually or concurrently, two markers unique to human urine. The testing regimen can utilize reagent systems for determining whether a urine sample, usually one submitted for drugs-of-abuse (DOA) testing, is true urine—of human origin—or a counterfeit (artificial) urine product.

More specifically, the subject invention provides a method and corresponding reagents for detecting the presence of two markers as determinants of whether a sample is true urine or a counterfeit urine product. The assay techniques of the subject invention employ acid phosphatase (AP) and alkaline phosphatase (ALP), two markers that are normally present in true urine, which react with specific substrates to provide a qualitative indication of the constitution of the sample. Preferred embodiments of the subject invention utilize a unique combination of testing and a control methodology by which an absence of the markers is detected, thereby indicating that the sample is not true urine and potentially a counterfeit urine product.

Advantageously, these markers have a labile nature that makes them unsuitable, or at least impractical, as additives to counterfeit urine products. The constituents are temperature sensitive causing them to degrade within a few days and become undetectable, often before the counterfeit urine product can be used. The reagents according to the subject invention are safe and non-toxic.

The embodiments of the subject invention are further advantageous in that they can be formulated as dip stick tests, as well as for use with automated laboratory equipment, such as clinical analyzers, particularly spectrophotometric-based analyzers. The use of automated laboratory equipment can make analysis of numerous samples more efficient, economical, and accurate, while a dipstick method can be useful for quick confirmatory tests, often where fewer samples need to be tested.

The markers AP and ALP have significantly different labilities, in that, they degrade at different rates. The lability of a sample is further affected by the temperature at which the sample is stored. Even ambient temperatures, for more than one day, can begin to affect the markers and other constituents, including DOA, in the sample. The common rule of thumb is that a 10° C. increase doubles the normal rate of decomposition of a sample and a 10° C. decrease reduces decomposition to about half the normal rate. Thus, a sample of urine, and the constituents and any DOA therein, would be expected to remain stable for about three days if kept at 2-10° C. A urine sample maintained at an ambient temperature of about 20-30° C. would be expected to remain stable for about one day.

The Food and Drug Administration has established c-GMP guidelines for DOA testing protocols, which are required to be followed by certified testing laboratories. One criteria is that samples be tested within established time frames. The testing methodology of the subject invention can be used to determine the age of a urine sample. AP normally degrades at a faster rate than ALP in a urine sample. The reagent systems of the subject invention can be used to detect the presence of both markers, AP and ALP, and include a control that can indicate whether the sample was adulterated. If the results of the assay show the presence of both AP and ALP and the control does not indicate tampering, i.e., no change in color of the control, then the sample is likely true urine and was recently collected and/or properly handled and stored. If the results of the assay show the presence of ALP, does not show the presence of AP, and the control does not indicate tampering, then it is likely that the sample is true urine, but was collected too long before the test was conducted and the AP has degraded to a point of non-detection. Alternatively the sample was improperly handled and/or stored.

Human urine has high concentrations of acid phosphatase and alkaline phosphatase. There are a number of substrates that are catalyzed by either acid or alkaline phosphatase. The substrates p-nitrophenyl phosphate and thymolphthalein monophosphate are unique because they are each catalyzed by AP and/or ALP and both have alkaline-activated chromogens, as illustrated in the following Table 1.

jected to alkaline conditions, thymolphthalein exhibits a blue color. Thymolphthalein monophosphate is catalyzed to form thymolphthalein as follows (Equation I):

Equation I

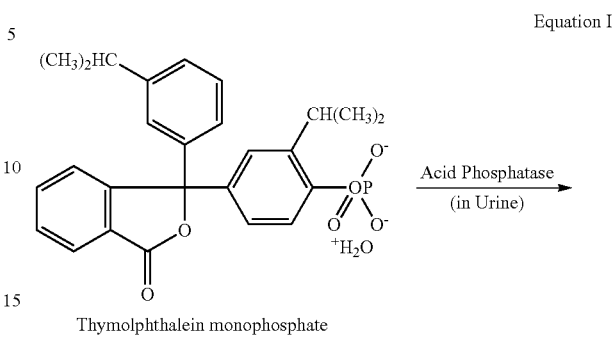

TABLE 1

Substrates for use in Detecting Acid and Alkaline Phosphatases

| Substrate | Chromogen Alkaline pH activated? | Reacts with Urinary Acid Phosphatase? | Reacts with Urinary Alkaline Phosphatase? | Color Indication (Absorbance nm) |
|---|---|---|---|---|
| p-nitrophenyl phosphate | Yes | Yes | Yes | Yellow (405-410) |
| Thymolphthalein monophosphate | Yes | Yes | +/− | Blue (600) |
| b-napthol phosphate | Yes | Yes | +/− | Yellow (410) or red (540) with diazo |
| phenolphthalein monophosphate | Yes | +/− | +/− | Red (540) |
| phenol phosphate | No | Yes | Yes | Red (540) with diazo or blue (600-700) with Folin reagent |
| glycerol phosphate | No | Yes | Yes | Yellow (410) (or blue 600-700 with additional reagent) |

The subject invention utilizes the urine markers acid phosphatase (AP) and alkaline phosphatase (ALP) as catalysts for two substrates that are each hydrolyzed under distinctly different pH conditions. The substrate thymolphthalein monophosphate is hydrolyzed by and preferred for detecting AP. Conversely, the substrate p-nitrophenyl phosphate is hydrolyzed by either the AP or ALP markers and is employed by the embodiments of the subject invention for detecting alkaline phosphatase. Testing for AP is preferred for samples that are relatively fresh, i.e., one to two days old, and testing for ALP is preferred for samples that are a few days older.

The substrate thymolphthalein monophosphate is shown below:

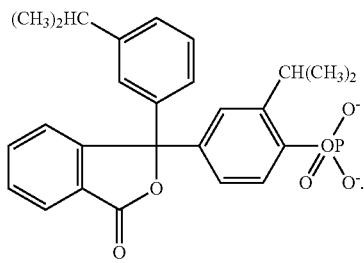

Thymolphthalein monophosphate is catalyzed by AP at between approximately pH 4 to approximately pH 6. When combined with an aliquot of a sample of true urine, AP in the urine hydrolyzes this substrate thereby producing free thymolphthalein. Thymolphthalein is a colorless product at the acid pH necessary for hydrolysis. When exposed or sub- -continued

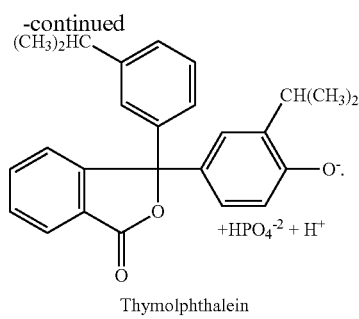

Thymolphthalein

Another substrate utilized with embodiments of the subject invention is p-nitrophenylphosphate:

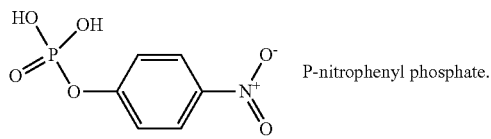 [SMILES: O=[N+]([O-])c1ccc(OP(=O)(O)O)cc1]

P-nitrophenyl phosphate.

P-nitrophenyl phosphate is catalyzed by urinary alkaline phosphatase (ALP) at between approximately pH 8 and approximately pH 11. P-nitrophenyl phosphate is also catalyzed by urinary acid phosphatase at between approximately pH 5 and approximately pH 6. When added to a sample of true urine, alkaline phosphatase (ALP) in the urine hydrolyzes the p-nitrophenol phosphate substrate, thereby producing free p-nitrophenol. P-nitrophenol turns yellow at the pH necessary for hydrolysis, thus is self-indicating. Acid phosphatase (AP) also catalyzes the hydrolysis of p-nitrophenol phosphate to liberate p-nitrophenol, which under the acid is colorless at the acid pH required for this AP reaction. Thus, a second step that alkalinizes the solution is necessary to activate p-nitrophenol as a chromagen that indicates the hydrolysis of p-nitrophenyl phosphate.

P-nitrophenylphosphate is catalyzed by ALP as follows (Equation II)

Equation II

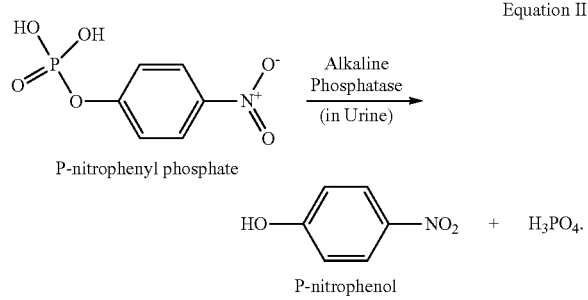

Thus, both thymolphthalein and p-nitrophenol are chromogens that are color-activated under alkaline conditions, such that thymolphthalein turns blue and p-nitrophenyl turns yellow.

Automated analyzers typically utilize liquid reagents that are robotically added to sample vials. In one embodiment, the reagents of the subject invention are formulated as liquids for use in an automated analyzer. When a sample treated according to the subject invention is analyzed spectrophotometrically, the blue color produced by thymolphthalein is absorbed at a wavelength of approximately 600 nm. The yellow color produced by p-nitrophenol is absorbed at a wavelength of between approximately 405 nm and approximately 410 nm.

The stability of the thymolphthalein monophosphate and p-nitrophenyl phosphate substrates makes them useful for dip stick or spot tests. Spot tests are well-known in the art and can have a liquid, semi-solid, or solid transport medium. For the sake of providing a visual representation of the embodiments of the subject invention, reference will be made to a dipstick methodology, as shown in FIGS. 1, 2, and 3. The ability to formulate the substrates of the subject invention for dipstick spot tests is known in the art and will not be described in detail here.

In one embodiment, the spot test is a paper strip or what is often referred to as a "dip stick." The dip stick can be prepared with "spots" or areas thereon comprising the corresponding substrate reagents or control reagent. In one embodiment, the p-nitrophenyl phosphate is present on a Test spot in at least five times the concentration utilized in the liquid reagent form. In another embodiment, the thymolphthalein monophosphate is present on a Test spot in at least five times the concentration utilized in the liquid reagent form. In a further embodiment, a Control spot has approximately 5% Brij 35, which is greater than the percentage used in the liquid reagent.

According to embodiments of the subject invention, a dip stick is treated with thymolphthalein monophosphate, p-nitrophenyl phosphate, or both, as shown in FIGS. 1, 2, and 3. The reagents can be deposited and the substrates stabilized in separate spots on the dip stick. To test a urine sample, the prepared spots on the dip stick are saturated with an aliquot of the sample. One or more of the sample-saturated spots are subsequently treated with an alkaline reagent to activate the chromogens.

Embodiments of the subject invention utilize reagent systems, which include substrate reagents that are catalyzed by either AP and/or ALP and a color-developer reagent that activates or enhances the appearance and color of the resulting chromogen. The reagent system embodiments can also utilize a control reagent, which advantageously confirms the presence or absence of one or both of the chromogens.

The reagent systems of the subject invention are effective when utilized individually to indicate the presence of one or both urine-related markers. The reagent systems can be most advantageous when utilized concurrently, as part of dual reagent system, because they provide a definitive, qualitative indication that a sample comprises true urine or a counterfeit urine product.

A further advantage of the reagent systems of the subject invention is the ability to determine the age of a urine sample, which can be used to indicate the viability of the sample and, further, the reliability of test results conducted on a sample. Testing laboratories can also utilize the results of such aging results to confirm that their sample handling protocols meet FDA guidelines.

One embodiment of a reagent system includes a substrate reagent comprising the substrate p-nitrophenyl phosphate that is buffered to between approximately pH 9.5 to approximately pH 11, which promotes formation of the chromogen in the presence of the catalyst. In a further embodiment, the reagent system includes a control reagent, which comprises no p-nitrophenol or p-nitrophenyl phosphate. The control reagent can also comprise all or most of the constituents of the substrate reagent, except for the substrate and the chromogen. In a yet further embodiment, the p-nitrophenyl phosphate reagent system has an alkaline color-developer reagent buffered to between approximately pH 9.5 to approximately pH 11. The color-developer reagent can be utilized with the control to determine whether a sample is true urine or a counterfeit urine product. This reagent system can be solidified and stabilized for use as dipstick method or the reagent system can be in liquid forms for use in clinical analyzers.

FIG. 1 illustrates a non-limiting example of a dip stick on which the substrate reagent and the control reagent have been stabilized on specific areas or "spots." In one embodiment, the substrate reagent is stabilized in a fashion that will provide the necessary alkaline pH for the substrate to be catalyzed, upon addition of true urine.

FIG. 1 illustrates a non-limiting example wherein the p-nitrophenol phosphate reagent system is utilized with a dip stick method. In the dip stick example shown in FIG. 1, the upper Test spot comprises the substrate reagent and the lower Control spot comprises the control reagent, which are, initially, colorless. When the spots are saturated with a sample, several reactions can occur, depending upon the constitution of the sample. True urine causes the upper Test spot to turn a distinctive yellow color, by the reaction of the ALP in the urine with the p-nitrophenyl phosphate, which cleaves the phosphate moiety, leaving the chromogen p-nitrophenol. When saturated with true urine, the Control spot remains colorless or can appear to turn the same color of the sample. The Control spot, at this point, does not have the same yellow color as the Test spot. The addition of other ingredients to a sample can cause the same result as true urine, i.e., turn the Test spot yellow. Advantageously, the color-developer reagent of the subject invention can detect these other potential additives, if present.

With regard to FIG. 1, to confirm whether the constitution of the sample is true urine or a counterfeit urine product, the Control spot is treated with the color-developer reagent of the p-nitrophenyl phosphate reagent system, which changes the Control spot to an alkaline pH. If, after addition of the color-developer reagent, the Control spot turns the same or a similar yellow color as the Test spot, it indicates that the p-nitrophenol chromogen was likely added to the sample, which further indicates the sample being a counterfeit urine product or was at least subject to other tampering.

With this embodiment of the p-nitrophenyl phosphate reagent system, it is also possible to detect the presence of thymolphthalein that may have been added to the sample. If the Test spot and/or the Control spot turn blue, as shown in FIG. 1, it indicates that thymolphthalein was added to the sample, which reacts, at least mildly, in the alkaline pH of the Test spot, such that both spots are imbued with a blue color. Addition of the second, alkaline color-developer reagent to the Control spot can turn it blue, providing further indication that thymolphthalein was likely added to the sample, as indicated in FIG. 1. If the Test spot and/or the Control spot turns green, both p-nitrophenol and thymolphthalein were added to the sample, whereby the color transformations of the yellow and blue chromogens combine to forms the green color, as also shown in FIG. 1.

Efforts to defeat the above-described testing methodology for detection of p-nitrophenyl phosphate can include the addition of indicator dyes, such as, for example, Alazrin yellow and Orange II. These indicator dyes can be added to counterfeit urine products to try to mimic the yellow/orange color of the p-nitrophenol chromogen, thus giving a false-positive indication of true urine. Alazrin yellow GG and Orange II are virtually colorless at normal acid pH of urine and most known counterfeit urine products. Their color is activated under alkaline conditions. Advantageously, the Control test and alkaline color-development reagent employed by the subject invention can reveal the use of these dyes, thereby providing basis to suspect a counterfeit urine product.

The p-nitrophenyl phosphate reagent system for detection of ALP, according to the subject invention, can also be formulated as liquid reagents to be employed in chemical analyzers. When employed with a chemical analyzer, the true urine sample and a sample adulterated with an indicator dye show a distinct difference in the response times for spectrographic absorption. This difference in response times and levels can be indicative of whether a sample has been adulterated with an indicator dye. Example 3 herein provides examples of liquid reagent compositions formulated for use in clinical analyzers, which includes an alkaline-buffered Component A and a substrate-containing Component B for color-development of the chromogen p-nitrophenol.

With reference to FIGS. 4 and 5, a true urine sample and a sample of counterfeit urine product with an indicator dye are tested in a clinical analyzer. Clinical analyzers will often warm a sample batch to body temperature (37° C.), as shown in FIGS. 4 and 5, which can take several seconds, e.g., between 8 and 16 seconds for some analyzers, before conducting tests. An absorption reaction during this warming-up phase can be indicative of a counterfeit urine product, particularly after addition of Component A, which lacks the substrate, is added to the sample.

It can be seen in FIG. 4 that when true urine is tested for ALP, using the reagents in Example 3 in a clinical analyzer, Component A can be added to the sample and there will be minimal or no change in the spectrographic absorption of the sample during the warming up phase. This is because Component A, a buffered alkaline solution, does not contain the p-nitrophenyl phosphate substrate to react with the ALP in the urine. At the end of the warming up phase, Component B, which does contain the substrate, can be added to the sample. As seen in FIG. 4, there is a short-duration spike in the absorbance at 405 nm after addition of Component B. This is due to normal degradation of the substrate, which forms a small amount of free p-nitrophenol chromogen. This free p-nitrophenol will react quickly under the alkaline conditions in the sample, due to Component A. After this initial spike, the absorbance rate at 405 nm (wavelength for detecting p-nitrophenol) shows a slow, generally linear increase as the substrate is catalyzed by the ALP in the urine sample. It can be seen that the maximum absorption level is approximately 50-65% of the maximum detectable absorbance.

It can be seen in FIG. 5 that the reaction of a counterfeit urine sample containing an alkaline-activated indicator dye subjected to the same testing protocol is noticeably different than that of the true urine sample. FIG. 5 shows that a counterfeit urine sample with an alkaline-activated indicator dye causes an immediate and significantly higher absorption rate than that shown by a true urine sample. This is caused by the alkalinity of Component A that immediately activates an alkaline-activated indicator dye. When Component B is added to the sample of counterfeit urine, there is a short-duration spike in the absorbance rate. As mentioned above, this is due to normal degradation of the substrate in Component B, which forms a small amount of free p-nitrophenyl chromogen. The reaction of this free p-nitrophenol increases the absorption levels. After the short-duration spike, the absorption at 405 nm is near maximum detectable levels, as seen in FIG. 5. Thus, from these examples shown in FIGS. 4 and 5, it can be seen that the differences in the absorbance times and levels between a true urine sample and that of a counterfeit urine product allow the p-Nitrophenyl phosphate reagent system embodiments of the subject invention to be used in a clinical analyzer to detect a counterfeit urine sample that includes an indicator dye.

In one embodiment, a clinical analyzer can be configured with protocols that indicate a positive result for adulteration when a sample shows an immediate absorbance during the initial warming up cycle. In a further embodiment, a clinical analyzer can be configured with protocols that indicate a positive result for adulteration when a sample shows an absorbance level that is above between approximately 50% and approximately 65% of the maximum detectable absorption at 405 nm. Because of the spike in absorbance that can result when Component B is added to a sample, as discussed above, the protocols of a clinical analyzer can also be configured to indicate a result after Component B is added to the sample. Thus, the testing period during which the protocols of a clinical analyzer will evaluate a sample can occur after the addition of Component B.

In another embodiment of a reagent system, a substrate reagent that comprises thymolphthalein monophosphate and is buffered to between approximately pH 4 and approximately pH 6 reacts with AP to promote the formation of the chromogen thymolphthalein. At this pH, there will typically be no formation of the color of the chromogen. In a further embodiment, the thymolphthalein monophosphate reagent system has a color-developer reagent having an alkaline pH of between approximately 9.5 to approximately 11. This can be similar to the color developer reagent utilized with the p-nitrophenyl phosphate substrate reagent, described above. In one embodiment, the control reagent utilized with this embodiment of the reagent system can comprise all or most of the constituents of the substrate reagent, but no thymolphthalein monophosphate substrate, nor any thymolphthalein, which is the chromogen formed from p-nitrophenyl phosphate when catalyzed with AP.

FIG. 2 illustrates a non-limiting example of a dip stick on which the substrate reagent and the control reagent have been stabilized onto specific test spots on the dipstick. In one embodiment, the first substrate reagent is stabilized in a fashion that will provide the necessary acidic pH for the substrate to be catalyzed upon addition of true urine. It will be understood by a person skilled in the art that this reagent system can be in liquid form and the method can be utilized with automated chemical analyzers. With regard to FIG. 2, which shows a non-limiting example of a dip stick method, the upper Test spot comprises the substrate reagent and the lower Control spot comprises the control reagent, which are both initially colorless. When the spots are saturated with a sample, several reactions can occur depending upon the nature of the sample. True urine causes the Test spot to turn a blue color, due to reaction of the AP in the urine with the p-nitrophenyl phosphate, which cleaves the phosphate moeity, leaving the chromogen p-nitrophenol. When saturated with true urine, the Control spot remains colorless or appears as the same color as the sample, e.g., pale yellow, but does not have the same blue color as the Test spot. However, the addition of other ingredients to a sample can cause the same results as true urine. Advantageously, the color-developer reagent of the subject invention can detect whether these other ingredients have been added to the sample.

With regard to FIG. 2, when the Test spot and Control spot are treated with the color-developer reagent of the reagent system, the Test spot and Control spot are changed to an alkaline pH, thereby activating the color change of the thymolphthalein to blue. If, after addition of the color-developer reagent, the Test spot turns blue and the Control spot remains colorless, it indicates that the sample was true urine and thymolphthalein liberated from the thymolphthalein monophosphate substrate was present on the Test spot. If, after addition of the color-developer reagent, neither the Test spot, nor and the Control spot turn blue, it indicates that the sample did not contain AP to react with the thymolphthalein monophosphate substrate. This can indicate that the sample was a counterfeit urine product or was otherwise subject to tampering. Counterfeit urine products or other tampering of the sample can also be suspected if, after addition of the color-developer reagent, the Control spot turns the same or a similar blue color as the Test spot, an indication that the thymolphthalein chromogen was added to the sample.

Furthermore, with this embodiment of the reagent system, it is possible to detect the presence of p-nitropheneol that may have been added to the sample. If, after addition of the color-developer reagent the Test spot and/or the Control spot turn yellow, as shown in FIG. 2, it can be an indication that p-nitrophenol was likely added to the sample. If the Test spot and/or the Control spot turns green, it can be an indication that both p-nitrophenol and thymolphthalein were likely added to the sample, whereby the color transformations of the yellow and blue chromogens combine to form the green color, as also shown in FIG. 2.

In yet another embodiment, the reagent systems described above for detecting alkaline and acid phosphatase are employed concurrently, as part of a dual reagent test conducted in a single test methodology. This embodiment utilizes both substrate reagents, one containing the substrate thymolphthalein monophosphate, buffered to between approximately pH 4 and approximately pH 6, and the other containing the substrate p-nitrophenyl phosphate, buffered to between approximately pH 9.5 and approximately pH 10. The pH of each reagent promotes the catalysis of the substrates to form the respective chromogens, as discussed above. In a further embodiment, a Control reagent is utilized to detect whether one or both chromogens were added to a sample.

FIG. 3 illustrates a non-limiting example of a dip stick on which the reagents and the Control have been stabilized onto specific spots on the dipstick. In one embodiment, the reagents are stabilized in a fashion that will provide the necessary pH for the substrate to be catalyzed. A person of skill in the art will understand that same reagent system can be prepared in liquid form and the method can be utilized with automated chemical analyzers. In one embodiment, shown with the dip stick example in FIG. 3, the ALP Test spot has the first substrate reagent comprising p-nitrophenyl phosphate. The AP Test spot has the second reagent comprising thymolphthalein monophosphate. In a further embodiment, the Control spot comprises the Control reagent that has neither the substrates nor the chromogens. Initially, all three spots are colorless. The combination of all three spots provides a cross-check test for determining if a sample lacks either of the substrates thymolphthalein monophosphate or p-nitrophenyl. This embodiment also acts as a cross-check test to determine whether the sample has been adulterated with either the thymolphthalein or the p-nitrophenol chromogens. This dual reagent test and the testing methodology can also be used to determine the general age of a sample by whether or not the control indicates true urine and whether one or both of the chromogens are detected, which is discussed below.

With the concurrent testing methodology, when the spots are saturated with an aliquot of the sample, several reactions can occur, depending upon the nature of the sample. True urine initially turns the ALP spot yellow, caused by the ALP in the urine that catalyzes the p-nitrophenyl phosphate, which cleaves the phosphate moiety, leaving the chromogen p-nitrophenol. As discussed above, p-nitrophenol is self-indicating, in that the alkaline pH required for catalysis also activates the yellow color of the p-nitrophenol. When saturated with true urine, the AP spot and the Control spot remain colorless or can take on the same color as the sample, e.g., pale yellow. As with the embodiments described above, the possible addition of other ingredients to the sample can cause the same result of turning the ALP spot yellow. The color-developer reagent of the subject invention can be used advantageously with the Control reagent to detect these other ingredients.

Referring to FIG. 3, when the AP Test spot and Control spot are treated with the color-developer reagent of this reagent system, the AP Test spot and Control spot change to an alkaline pH. If, after addition of the color-developer reagent, the AP Test spot turns blue and the Control spot remains colorless, it indicates that the sample was true urine and thymolphthalein liberated from the thymolphthalein monophosphate substrate was present on the AP Test spot.

Thus, with the dual reagent system test and the testing methodology of this embodiment, true urine turns the ALP spot yellow, the AP spot blue, and the Control remains uncolored. Any other result than this can indicate that the sample is not true urine and either lacks one or both of the markers or has been adulterated likely by addition of one or both of the chromogens, or that the sample is too old or was improperly handled to provide reliable results. For example, if the ALP Test spot initially turns blue, it can indicate that the sample was adulterated with thymolphthalein, which was activated by the alkalinity of the ALP spot and not by reaction of the substrate. If, after addition of the color-developer reagent, neither the AP Test spot, nor the Control spot turn blue, the sample did not contain AP to react with the thymolphthalein monophosphate substrate. This can indicate that the sample was a counterfeit urine product or was otherwise subject to tampering, even if the ALP spot turned yellow, because true urine typically contains both AP and ALP catalysts. Counterfeit urine product or other tampering of the sample can also be suspected if, after addition of the color-developer reagent, the Control spot turns yellow or blue, an indication that the p-nitrophenol or thymolphthalein chromogen was likely added to the sample. Furthermore, if either or both the AL Test spot, the ALP Test spot, and/or the Control spot turns green, it can be an indication that both p-nitrophenol and thymolphthalein were likely added to the sample, whereby the color transformations of the yellow and blue chromogens combine to form the green color, as also shown in FIG. 3. A sample that is more than 3 days old or that has been improperly handled and/or stored can provide unreliable results. Advantageously, the concurrent testing methodology of the subject invention, utilizing a dual reagent system, provides a convenient method for determining the general age or condition of a sample. Specifically, detection of the ALP marker in the absence of detection of the AP marker and a control that indicates the sample is true urine can indicate that the sample is too old, such that the AP marker has degraded beyond detectable levels or that the sample was improperly handled and/or stored, such that the AP marker degraded prematurely. Either situation would indicate a sample of dubious integrity and one that is incapable of providing reliable test results.

Another result that can occur is the detection of one of the markers and no change in the color of the Control. More specifically, the detection of ALP, without a change in the color of the control can be obtained. Such results can indicate that the sample is true urine, but is too old or "aged" beyond a viable testing period. For example, if the testing protocol for concurrently detecting AP and ALP is utilized, a urine sample that is sufficiently fresh or that has been maintained under appropriate refrigerated conditions will produce a yellow ALP test spot, a blue AP test spot, and no change in the Control spot. If the same testing protocol is used and the urine sample is more than 2-3 days old or has not been stored under appropriate refrigeration, the ALP test spot will turn yellow, the AP test spot will show no change in color and no change in the Control spot. Furthermore, if the same testing protocol is used and there is no change in any of the spots it is an indication that either the sample is not true urine or that the sample is true urine that has aged beyond the point of obtaining any reliable test results.

The scope of the invention is not limited by the specific examples and suggested procedures and uses related herein since modifications can be made within such scope from the information provided by this specification to those skilled in the art.

A more complete understanding of the invention can be obtained by reference to the following specific examples of reagents and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available, preferably ACS grade, from known sources, e.g., chemical supply houses, so no details are given respecting them.

Example 1: Preparation of Reagent System for Detection of Thymolphthalein Using Automated Analyzers

| Substrate Reagent: comprises Component A and Component B, which are added in a 50/50 ratio to obtain the final concentration: | | | |
|---|---|---|---|
| Component A: | 17.68 | grams | Sodium Acetate, added to approximately 400 mL deionized water and mix until dissolved |
| | 1.6 | grams | Citric Acid followed with sufficient Acetic Acid (redistilled) to adjust pH to 5.6 @ 25° C. |
| | 0.2 | grams | Proclin 300 |
| | Add deionized water to obtain final volume of 500 mL | | |
| Component B: | 5.0 | grams | Brij 35 detergent, added to 500 mL deionized water and mix until dissolved |
| | 1.0 | grams | Thymolphthalein monophosphate sodium salt and mix until dissolved |

Combine equal parts of Component A and Component B to obtain a final solution of Substrate Reagent. For example, 500 mL of Component A can be combined with 500 mL of Component B to obtain 1 liter of Substrate Reagent. The Substrate Reagent should be stored refrigerated at between 4°-8° C., away from light.

| Color-Developer reagent: | 20 grams | Sodium Hydroxide |
|---|---|---|
| | 53 grams | Sodium Carbonate (Anhydrous) |
| Combine with 1 liter of deionized water to obtain final concentration and volume. | | |
| Control Reagent: 500 mL of deionized water and 500 mL of Component B added. | | |
| Calibrator: | 100 Units | Urinary Tract Protein |
| | 700 mL | n-propanol |
| | 300 mL | Deionized water |
| | 20 mg | Thymolphthalein |

The Urinary Tract Protein Units are arbitrary and based upon the amount of thymolphthalein produced during the time of incubation of Component A with a given ratio of component A to urine. Thus, if the time of incubation is doubled, the value of the calibrator can be cut in half. If the urine volume to Component A is lowered by decreasing sample volume, the value can be increased proportionately. The arbitrary units are intended to avoid traditional enzyme measurement and the marker(s) are to be described as Urinary Tract Glyco-proteins, so as to obscure the identity of subversion additions to the counterfeit urine.

Example 2: Parameter Settings for Detection of Thymolphthalein Using Automated Clinical Chemistry Analyzers Following are specifications for testing a urine sample with a Mindray BS-200 automated chemical analyzer. These settings are intended as guidelines and those with skill in the art would recognize that the parameters can vary between instruments.

| Test: | TrueUrine |
|---|---|
| No. | User Defined |
| Full Name: | True Urine |

| | |
|---|---|
| Reaction Type: | Fixed-time |
| Pri. Wave | 578 nm |
| Sec Wave | 670 |
| Direction: | Increase |
| Reac. Time: | 0 and 2 |
| Incubation Time: | 20 |
| Unit: | UTP Units |
| Precision: | Integer |
| R1: | 180 |
| R2: | 40 |
| Sample Volume: | 46 |
| Mixed Reagent Blank: | |
| Compensate: | Slope:1 Intercept: 0 |

Following are specifications for testing a urine sample with the AU 400, AU 400e, AU 480, AU 640, AU640e and AU680 Series automated chemical analyzers. These settings are intended as guidelines and those with skill in the art would recognize that the parameters can vary between instruments.

| | |
|---|---|
| Reagent ID: | User defined |
| Test Name: | True Urine |
| Sample Volume: | 30 |
| R1 Volume: | 123 |
| R2 Volume: | 43 |
| Wavelength: Pri: | 600 Sec. 700 |
| Method: | FIXED TIME |
| Reaction Slope: | POS |
| Measuring Point 1: | First 14 Last 16 |
| Measuring Point 1: | (Not Applicable) |
| Calibration Type: | 2AB Formula: Polygonal |
| Point 1 H20 | CONC: 0 |
| Point 2 Cal | CONC: 100 |

Note: the control procedure is the same as the Test procedure.

Example 3: Preparation of Reagent System for Detection of p-Nitrophenol Using Automated Analyzers

| Substrate Reagent: Alkaline Buffered and a combination of the following Component A and Component B. | | |
|---|---|---|
| Component A: | 31 grams | 2-amino-2-methyl- 1-propanol (AMP) |
| | 0.2 grams | Proclin 300 |
| | 0.6 grams | N-hydroxyethylene-diaminetriacetic acid (HEDTA) |
| Combine the above ingredients with approximately 800 ml deionized water and mix to dissolve to form solution #1. | | |
| | 0.3 grams | Zinc Sulfate•7H$_2$O |
| Add to solution #1 and mix to dissolve to form solution #2. | | |
| | 0.4 grams | Magnesium Acetate•4H$_2$O |
| Add to solution #2 and mix to dissolve to form solution #3. | | |
| Adjust pH of solution #3 to 10.2 +/− 0.05 using 6 N HCl, to form solution #4. | | |
| | 4 grams | Brij 35 30% solution |
| Add to solution #4 and mix to dissolve to form solution #5. | | |
| Reagent #1 is formed by adding deionized water to solution #5 to make 1 Liter and mix to dissolve. Avoid excess exposure to air following pH adjustment. Note: This is a buffered solution. | | |
| Component B: | 900 mL | Deionized water |
| | 0.5 grams | Proclin 300 |
| | 2.0 grams | Imidazol |
| | 20 grams | p-nitrophenol phosphate disodium salt (hydrate form) CAS No. 123359-43-3 |
| Adjust to pH 6.5 +/− 0.01 with pure 6 N HCl and bring volume to 1000 ml with deionized water. | | |
| Control Reagent: Component A is replaced with deionized water and an alkaline solution, such as Component B of Example 1 above, is added as in the test. This type control is only required for dip-stick tests or where the reagent is measured as an end- | | |

| Substrate Reagent: Alkaline Buffered and a combination of the following Component A and Component B. | | |
|---|---|---| point assay. If the p-nitrophenol phosphate reagent is detected by an automated device as a fixed time or kinetic assay, the initial absorbance of the reagent may be observed as a control and limits set for the initial absorbance if permitted by the automated device. Otherwise, a control as provided above must be performed to detect addition of adulterants to the counterfeit urine.

| Calibrator: | 100 Units/L | Urinary tract Protein-LD |
|---|---|---|
| | 1.0 Liter | 50% Glycerol in Deionized water |
| | 1.6 grams | Tris Hydrochloride |
| | 0.3 grams | Magnesium Chloride |
| | 0.02 grams | Zinc Chloride |
| To the above solution add 50 Units of Alkaline phosphatase CAS RN 9001-78-9. | | |
| Stock Calibrator: | 140 mg | p-Nitrophenol |
| | 0.2 g | Proclin 300 |
| | 300 mg | Imidazol |

Combine with approximately 800 mL of deionized water and mix to dissolve. Adjust pH to 6.5 using diluted HCl. Final Calibrator is Stock Calibrator diluted 1:250 with deionized water to obtain a Final Calibrator solution having the equivalent of 100 Enzyme Units (Urinary Tract Protein). Note: An enzyme unit (U) is specific to particular enzyme and is defined as the amount of the enzyme that catalyzes the conversion of 1 micro mole of substrate per minute.

Example 4: Parameter Settings for Detection of p-Nitrophenol Using Automated Clinical Chemistry Analyzers Following are specifications for testing a urine sample with a Mindray BS-200 automated chemical analyzer. These settings are intended as guidelines and those with skill in the art would recognize that the parameters can vary between instruments.

| | |
|---|---|
| Test: | UALP |
| No. | User Defined |
| Full Name: | Alkaline Phosphatase |
| Reaction Type: | Fixed-time |
| Pri. Wave | 510 nm |
| Sec Wave | 630 |
| Direction: | Increase |
| Reac. Time: | 0 and 2 |
| Incubation Time: | 20 |
| Unit: | UALP Units |
| Precision: | Integer |
| R1: | 180 |
| Sample Volume; | 46 |
| Mixed Reagent Blank: | |
| Compensate: | Slope:1 Intercept: 0 |

Note: The control procedure for the above is the same as the test procedure, but uses the control reagents. The calibration for the above is the same as the test procedure.

Following are specifications for testing a urine sample with the AU 400, AU 400e, AU 480, AU 640, AU640e and AU680 Series automated chemical analyzers. These settings are intended as guidelines and those with skill in the art would recognize that the parameters can vary between instruments.

| | |
|---|---|
| Reagent ID: | User defined |
| Test Name: | True Urine LD |
| Sample Volume: | 35 |

-continued

| | |
|---|---|
| R1 Volume: | 120 |
| R2 Volume: | 30 |
| Wavelength: Pri: | 405 Sec. — |
| Method: | FIXED TIME |
| Reaction Slope: | POS |
| Measuring Point 1: | First 13 Last 27 |
| Units: | UTP Units |
| Calibration Type: | AA Formula: Y = AX + B |
| Point 1 | CONC: 0 |
| Point 2 | CONC:100 |

Note:
The control procedure for the above is the same as the Test procedure, but uses Control Reagent #1.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. A reagent system, utilized to detect markers in a urine sample, the reagent system comprising:
   a first substrate reagent having an alkaline pH that comprises zinc sulfate and p-nitrophenyl phosphate substrate, which is catalyzed by a first marker in the urine sample to produce a chromogen that forms a first color in a first reacted sample;
   a second substrate reagent having an acid pH that comprises citric acid and thymolphthalein monophosphate substrate, which is catalyzed by a second marker in the urine sample to produce a chromogen in a second reacted sample;
   a liquid color-developer having an alkaline pH that activates the chromogen in the second reacted sample to form a second color; and
   a control reagent having an acid pH and comprising citric acid.

2. The reagent system, according to claim 1, wherein the marker in the urine that catalyzes the first substrate is alkaline phosphatase.

3. The reagent system, according to claim 2, wherein the marker in the urine that catalyzes the second substrate is acid phosphatase.

4. The reagent system, according to claim 1, wherein the first color is spectrophotometrically measurable at between approximately 405 nm and approximately 410 nm.

5. The reagent system, according to claim 4, wherein the second color is spectrophotometrically measureable at approximately 600 nm.

6. The reagent system, according to claim 1, further comprising a dipstick on which the first substrate reagent of the reagent system is stabilized in a first test spot, the second substrate reagent of the reagent system is stabilized in a second test spot, and the control reagent is stabilized in a third test spot.

7. A method for verifying a urine sample is human-derived, the method comprising:
   a) obtaining a reagent system, according to claim 1;
   b) combining an aliquot of the urine sample with the first reagent of the reagent system, to form a chromogen in a first reacted sample;
   c) combining an aliquot of the urine sample with the second reagent of the reagent system, to form a chromogen in a second reacted sample;
   d) combining an aliquot of the urine sample with the control reagent of the reagent system in a third reacted sample;
   e) observing the formation of a yellow color in the first reacted sample;
   f) combining the color-developer with the second reacted sample;
   g) observing the formation of a blue color in the second reacted sample;
   h) combining the color-developer with the third reacted sample; and
   i) observing a lack of color formation in the third reacted sample, such that formation of the yellow color in the first reacted sample, formation of the blue color in the second reacted sample, and the lack of color formation in the third reacted sample is indicative of a human-derived urine sample.

8. The method, according to claim 7, wherein the first substrate comprising p-nitrophenyl phosphate catalyzes to the chromogen p-nitrophenol.

9. The method, according to claim 8, wherein the second substrate comprising thymolphthalein monophosphate catalyzes to thymolphthalein.

10. The method, according to claim 9, wherein a marker in the urine sample that catalyzes the second substrate is acid phosphatase.

11. The method, according to claim 10, wherein the reagent system further comprises a dipstick on which the first substrate reagent of the reagent system is stabilized in a first test spot, the second substrate reagent of the reagent system is stabilized in a second test spot, and the control reagent is stabilized in a third test spot and the method further comprises,
   adding an aliquot of the urine sample to each of the first test spot, the second test spot, and the third test spot,
   observing the formation of a yellow color at the first test spot,
   adding the color developer to the second test spot,
   observing the formation of a blue color at the second test spot,
   adding the color developer to the third test spot,
   observing a lack of color formation at the third test spot, such that formation of the yellow color at the first test spot, formation of the blue color at the second test spot, and the lack of color formation at the third test spot is indicative of a human-derived urine sample.

12. The method, according to claim 8, wherein a marker in the urine sample that catalyzes the first substrate is alkaline phosphatase.

13. A dual reagent system, utilized to detect two markers in a urine sample, the dual reagent system comprising:

a liquid first substrate reagent having an alkaline pH and comprising:
   a first component that comprises zinc sulfate,
   a second component that comprises p-nitrophenyl phosphate substrate, which is catalyzed by a first marker in the urine sample to form a first color;
a liquid second substrate reagent having an acid pH and comprising citric acid and thymolphthalein monophosphate substrate, which is catalyzed by a second marker in the urine sample to form a chromogen;
a liquid color-developer reagent having an alkaline pH that activates the chromogen to form a second color; and
a control reagent comprising citric acid.

14. The reagent system, according to claim 13, wherein the marker in the urine that catalyzes the liquid first substrate is alkaline phosphatase.

15. The reagent system, according to claim 14, wherein the marker in the urine that catalyzes the liquid second substrate is acid phosphatase.

* * * * *